(12) United States Patent
Ramachandran et al.

(10) Patent No.: US 10,317,197 B2
(45) Date of Patent: Jun. 11, 2019

(54) SYSTEM AND METHOD FOR STABILIZING OPTICAL SHAPE SENSING

(71) Applicant: KONINKLIJKE PHILIPS N.V., Eindhoven (NL)

(72) Inventors: Bharat Ramachandran, Morganville, NJ (US); Robert Manzke, Bönebüttel (DE); Raymond Chan, San Diego, CA (US)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 14/397,789

(22) PCT Filed: May 1, 2013

(86) PCT No.: PCT/IB2013/053444
§ 371 (c)(1),
(2) Date: Oct. 29, 2014

(87) PCT Pub. No.: WO2013/168052
PCT Pub. Date: Nov. 14, 2013

(65) Prior Publication Data
US 2015/0124264 A1    May 7, 2015

Related U.S. Application Data

(60) Provisional application No. 61/644,474, filed on May 9, 2012.

(51) Int. Cl.
*G01B 11/24* (2006.01)
*G02B 6/02* (2006.01)
(Continued)

(52) U.S. Cl.
CPC ............ *G01B 11/24* (2013.01); *A61B 5/0059* (2013.01); *A61B 5/1076* (2013.01);
(Continued)

(58) Field of Classification Search
CPC .......... G01B 11/24; G01B 11/16; G02B 6/02; G02B 6/04; A61B 19/00; G01L 25/00
See application file for complete search history.

(56) References Cited

U.S. PATENT DOCUMENTS

| | | | |
|---|---|---|---|
| 7,542,856 | B2 | 6/2009 | Kishida et al. |
| 2008/0177482 | A1 | 7/2008 | Kishida et al. |

(Continued)

FOREIGN PATENT DOCUMENTS

| | | |
|---|---|---|
| CN | 101313847 A | 12/2008 |
| JP | 2010172425 A | 8/2010 |
| WO | 2011080606 A1 | 7/2011 |
| WO | 2012025856 A1 | 3/2012 |

OTHER PUBLICATIONS

Duncan et al, "Characterization of a Fiber-Optic Shape and Position Sensor", Proceedings of SPIE, vol. 6167, Feb. 27, 2006, XP-002616927, pp. 616704-1-616704-11.

(Continued)

*Primary Examiner* — Jamil Ahmed

(57) ABSTRACT

A system and method for shape sensing with optical fiber include collecting (610) shape data from a shape sensing optical fiber device. The shape data are tested (620) to determine data positions that exceed an acceptable threshold based on geometrical expectations of the shape data. The shape data corresponding to the data positions that exceed an acceptable threshold are rejected (640). Acceptable shape data are rendered (650) to provide a stable shape sensing data set.

19 Claims, 7 Drawing Sheets

(51) Int. Cl.
*G01B 11/16* (2006.01)
*A61B 5/107* (2006.01)
*G01B 21/04* (2006.01)
*A61B 6/00* (2006.01)
*A61B 5/00* (2006.01)
*A61B 5/055* (2006.01)

(52) U.S. Cl.
CPC .......... *A61B 5/1079* (2013.01); *A61B 6/5247* (2013.01); *G01B 11/16* (2013.01); *G01B 11/18* (2013.01); *G01B 21/04* (2013.01); *G02B 6/02076* (2013.01); *A61B 5/055* (2013.01); *A61B 5/7221* (2013.01)

(56) References Cited

U.S. PATENT DOCUMENTS

| | | | |
|---|---|---|---|
| 2011/0113852 A1* | 5/2011 | Prisco | A61B 19/2203 73/1.15 |
| 2011/0319910 A1* | 12/2011 | Roelle | A61B 19/2203 606/130 |
| 2013/0150732 A1 | 6/2013 | Manzke et al. | |

OTHER PUBLICATIONS

Zhang, L. et al., "Three dimensional curve reconstruction based on fiber Bragg grating sensors". Estimation Detection and Information Fusion, 2015 International Conference on Jan 0-11, 2015. China.

* cited by examiner

US 10,317,197 B2

SYSTEM AND METHOD FOR STABILIZING OPTICAL SHAPE SENSING

CROSS-REFERENCE TO PRIOR APPLICATIONS

This application is the U.S. National Phase application under 35 U.S.C. § 371 of International Application Serial No. PCT/IB2013/053444 filed on May 1, 2013, which claims the benefit of U.S. Application Ser. No. 61/644,474, filed on May 9, 2012. These applications are hereby incorporated by reference herein.

This disclosure relates to shape sensing instruments and more particularly to a system and method for use with shape sensing optical fibers having improved stability.

Shape sensing based on fiber optics exploits the inherent backscatter in a conventional optical fiber. The principle involved makes use of distributed strain measurement in the optical fiber using characteristic Rayleigh backscatter patterns.

A physical length and index of refraction of a fiber are intrinsically sensitive to environmental parameters, temperature and strain and, to a much lesser extent, pressure, humidity, electromagnetic fields, chemical exposure, etc. The wavelength shift, $\Delta\lambda$ or frequency shift, $\Delta v$, of the backscatter pattern due to a temperature change, $\Delta T$, or strain along the fiber axis, $\varepsilon$ is: $\Delta\lambda/\lambda = -\Delta v/v = K_T \Delta T + K_\varepsilon \varepsilon$, where $$K_\varepsilon = 1 - \frac{n_{eff}^2}{2}(p_{12} - v(p_{11} + p_{12})).$$

The temperature coefficient $K_T$ is a sum of the thermal expansion coefficient $\alpha = (1/\Lambda)(\partial\Lambda/\partial T)$ and the thermo-optic coefficient, $\xi = (1/n)(\partial n/\partial T)$, with a typical value of $0.55 \times 10^{-6}$ C.$^{-1}$ and a value of $6.1 \times 10^{-6}$ C.$^{-1}$ for germanium-doped silica core fibers. The strain coefficient $K\varepsilon$ is a function of group index n, the components of the strain-optic tensor, $p_{ij}$ and Poisson's ratio, $\mu$. Typical values given for n, $p_{12}$, $p_{11}$ and $\mu$ for germanium-doped silica yield a value for $K\varepsilon$ of about 0.787. Thus, a shift in temperature or strain is merely a linear scaling (for moderate temperature and strain ranges) of the spectral frequency shift $\Delta v$. Naturally, this linear model would not apply if strains approach the elastic limit of the fiber, or temperatures approach the glass transition temperature of the fiber.

With a four or more core fiber system where one core is located in a center of the cross-section, strain due to bending and temperature effects can be separated out as long as no axial strain (tension) is applied, or in the event axial strain is present, the axial strain is known and controllable (so it can be calibrated out).

Laser realignment is necessary from time to time for the optical system. The optical system needs to be calibrated with polarization states having a proper phase difference. This is performed for each of the cores (e.g., each of four cores). If any of these steps are not performed properly, then the optical sensing system may become unstable.

The strain and shape measurements reconstructed interferometrically from correlation and phase tracking need a fixed launch region, and a tether proximal to the launch region needs to be held steady. Any motion of these may result in shape instability. Wobble measurements define a characteristic of the fiber, and any mechanical compression, tension or pressure at any location on the fiber can change the mechanical properties and position of any of the cores. This may also change the backscatter pattern from the fiber and result in instability. The effect and instability due to axial tension/strain on the fiber also needs to be considered.

In accordance with the present principles, a system and method for shape sensing with optical fiber include collecting shape data from a shape sensing optical fiber device. The shape data are tested to determine data positions that exceed an acceptable threshold based on geometrical expectations of the shape data. The shape data corresponding to the data positions that exceed the acceptable threshold are rejected. Acceptable shape data are rendered to provide a stable shape sensing data set.

In one embodiment, a method for shape sensing with optical fiber includes collecting shape data from a shape sensing optical fiber device; removing outlier data from the shape data; testing the shape data to determine data positions that exceed acceptable thresholds based on geometrical expectations of the shape data, the testing includes one or more of: computing spatio-temporal continuity along the shape data; and computing a twist or a twist-derived parameter along the shape data. The shape data corresponding to the data positions that exceed acceptable thresholds are rejected, and acceptable shape data is rendered to provide a stable shape sensing data set.

In another embodiment, a shape sensing system includes a workstation configured to receive optical signals from a shape sensing enabled device having at least one optical fiber and to interpret the optical signals to determine a shape of the shape sensing enabled device. The workstation includes a processor and a memory coupled to the processor. A stability module is stored in the memory and configured to perform tests on the shape data to determine data positions that exceed an acceptable threshold based on geometrical expectations of the shape data, and reject the shape data corresponding to the data positions that exceed the acceptable threshold for rendering as a stable shape sensing data set.

These and other objects, features and advantages of the present disclosure will become apparent from the following detailed description of illustrative embodiments thereof, which is to be read in connection with the accompanying drawings.

This disclosure will present in detail the following description of preferred embodiments with reference to the following figures wherein.

Figure 1:
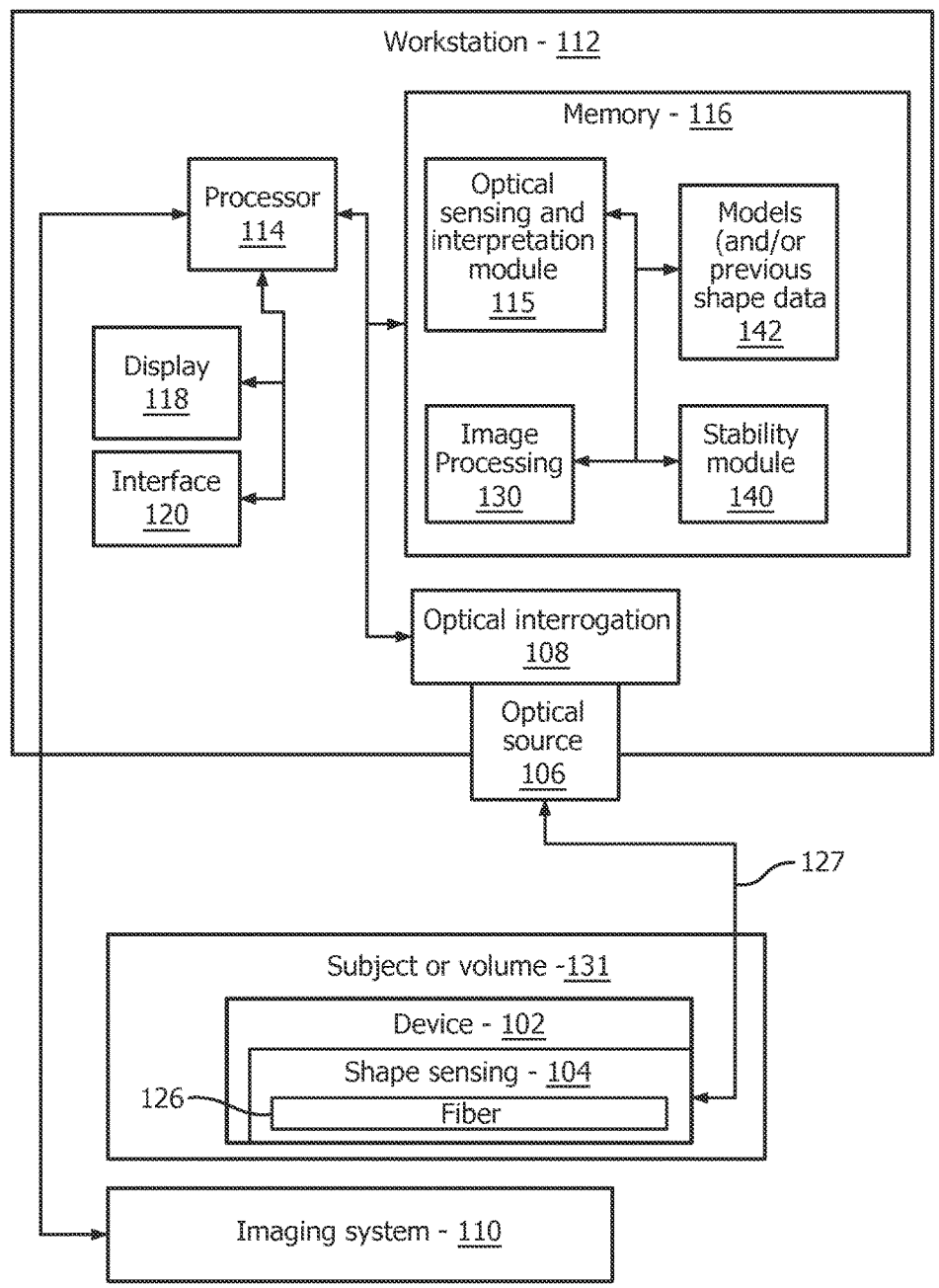
FIG. 1 is a block/flow diagram showing a shape sensing system which employs a stability module in accordance with one embodiment.

In accordance with the present principles, systems and methods for stable shape sensing are disclosed. Instability of shape sensing is a major problem and may arise due to different reasons. Examples of a few of reasons for unstable shape sensing may include loss of laser alignment; phase tracking failure; loss of correlation between a reference and sample arm; motion of a tether proximal to a launch region; improper calibration; variation in temperature (ambient as well as sharp local temperatures); local pressure/stress resulting in loss of original geometry of any of the fiber cores; high twist/roll (e.g., multiple π turns about the fiber's axis); high curvature; vibrations; axial tension, etc. The present embodiments provide methods for detection and correction of incorrect shapes during shape sensing. When correction is not possible (e.g., due to loss of phase tracking), erroneous shapes can be eliminated. The present embodiments overcome limitations of instability.

Optical shape sensing (OSS), while having the ability to deliver accurate shape reconstructions, can at times become unstable and reconstruct incorrect shapes. In accordance with the present principles, systems and methods detect, remove, or correct the inaccurate shapes and in the process, improve the stability and performance of OSS.

In one embodiment, a stability-enhancing method for OSS is provided that detects deviant or erroneous shapes and corrects the same. If correction is not possible, the erroneous shapes are eliminated and not displayed as output. The embodiments include detection and correction by using parameters that include but are not limited to: Cartesian space: nodal position, nodal velocity, and/or nodal acceleration; bend angle space: node angular velocity and/or node angular acceleration; twist/roll: node twist, cumulative twist and/or differentials of nodal twist; prior knowledge for exploiting spatio-temporal smoothness of instrument position, velocity, and acceleration; temporal filtering such as averaging; any other or any combination of the listed parameters. Methods using a combination of the above parameters are likely to yield better results. Furthermore, for example, when a portion of the shape (distal) is erroneous while the proximal shape is accurate, the methods can detect the fiber index/node where the low confidence measurement arises, display a portion of the shape and/or correct the remainder of the shape and display the same and/or display an earlier correct shape to substitute for the incorrect portion.

It should be understood that the present invention will be described in terms of medical instruments; however, the teachings of the present invention are much broader and are applicable to any fiber optic instruments. In some embodiments, the present principles are employed in tracking or analyzing complex biological or mechanical systems. In particular, the present principles are applicable to internal tracking procedures of biological systems, procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W), Blu-Ray™ and DVD.

Referring now to the drawings in which like numerals represent the same or similar elements and initially to FIG. 1, a system 100 for optical shape sensing is illustratively shown in accordance with one embodiment. System 100 may include a workstation or console 112 from which a procedure is supervised and/or managed. Workstation 112 preferably includes one or more processors 114 and memory 116 for storing programs and applications. Memory 116 may store an optical sensing and interpretation module 115 configured to interpret optical feedback signals from a shape sensing device or system 104. Optical sensing module 115 is configured to use the optical signal feedback (and any other feedback) to reconstruct deformations, deflections and other changes associated with a medical device or instrument 102 and/or its surrounding region. The instrument 102 may include a catheter, a guidewire, a probe, an endoscope, a robot, an electrode, a filter device, a balloon device, or other medical component, etc. In one embodiment, instrument 102 is simply an elongated flexible device including a plurality of optical fibers for conducting shape sensing. The instrument 102 is advanced into a volume or subject 131 to take on a shape which will be measured and corrected in accordance with the present principles.

The shape sensing system 104 on instrument 102 includes one or more optical fibers 126 which are coupled to the instrument 102 in a set pattern or patterns. The optical fibers 126 connect to the workstation 112 through cabling 127. The cabling 127 may include fiber optics, electrical connections, other instrumentation, etc., as needed.

Shape sensing system 104 with fiber optics may be based on fiber optic Bragg grating sensors. A fiber optic Bragg grating (FBG) is a short segment of optical fiber that reflects particular wavelengths of light and transmits all others. This is achieved by adding a periodic variation of the refractive index in the fiber core, which generates a wavelength-specific dielectric mirror. A fiber Bragg grating can therefore be used as an inline optical filter to block certain wavelengths, or as a wavelength-specific reflector.

A fundamental principle behind the operation of a fiber Bragg grating is Fresnel reflection at each of the interfaces where the refractive index is changing. For some wavelengths, the reflected light of the various periods is in phase so that constructive interference exists for reflection and, consequently, destructive interference for transmission. The Bragg wavelength is sensitive to strain as well as to temperature. This means that Bragg gratings can be used as sensing elements in fiber optical sensors. In an FBG sensor, the measurand (e.g., strain) causes a shift in the Bragg wavelength.

One advantage of this technique is that various sensor elements can be distributed over the length of a fiber. Incorporating three or more cores with various sensors (gauges) along the length of a fiber that is embedded in a structure permits a three dimensional form of such a structure to be precisely determined, typically with better than 1 mm accuracy. Along the length of the fiber, at various positions, a multitude of FBG sensors can be located (e.g., 3 or more fiber sensing cores). From the strain measurement of each FBG, the curvature of the structure can be inferred at that position. From the multitude of measured positions, the total three-dimensional form is determined.

As an alternative to fiber-optic Bragg gratings, the inherent backscatter in conventional optical fiber can be exploited. One such approach is to use Rayleigh scatter in standard single-mode communications fiber. Rayleigh scatter occurs as a result of random fluctuations of the index of refraction in the fiber core. These random fluctuations can be modeled as a Bragg grating with a random variation of amplitude and phase along the grating length. By using this effect in three or more cores running within a single length of multi-core fiber, the 3D shape and dynamics of the surface of interest can be followed.

Workstation 112 may include a display 118 for viewing internal images of a subject (patient, mechanical system, model or test platform, etc.), if an imaging system 110 is employed. The display 118 may be employed to view a rendering of shape data from the shape sensing system 104. Imaging system 110 may include a magnetic resonance imaging (MRI) system, a fluoroscopy system, a computed tomography (CT) system, etc. Display 118 may also permit a user to interact with the workstation 112 and its components and functions, or any other element within the system 100. This is further facilitated by an interface 120 which may include a keyboard, mouse, a joystick, a haptic device, or any other peripheral or control to permit user feedback from and interaction with the workstation 112. The shape sensing data and the imaging data may be registered as a method of verification for the shape sensing data. An image processing program 130 may be employed to permit manipulation of images and data to provide verification of the positional shape sensing data.

Workstation 112 includes an optical source 106 to provide optical fibers with light (e.g., laser light). An optical interrogation unit or module 108 is employed to detect light returning from all fibers. This permits the determination of strains or other parameters, which will be used to interpret the shape, orientation, or other characteristics, sensed by the system 104. The light signals will be employed as feedback to make adjustments to access errors and to calibrate the shape sensing system 104 or system 100.

In accordance with one embodiment, a stability module 140 is included in memory 116. The stability module 140 detects erroneous shapes, corrects the erroneous shapes, or, if correction is not possible, eliminates the shapes from displayed output. The stability module 140 detects errors and corrects shapes by employing parameters. The parameters described below may be employed together or separately. Each parameter set may be more adaptable to a given contortion or shape of the fiber, and different portions of the fiber may be described by different parameters to express the same shapes. Some of the parameters may include but are not limited to, e.g.:

Cartesion parameters, e.g., nodal position, nodal velocity, and/or nodal acceleration. Nodal position is a position at a node i and at time t=j, and can be given by $x_{i,j}$ along the length of the fiber. As the node increases, i increases from i=1 until a last index (e.g., N). Nodal position may be expressed as an equation, a string of segments or elements in a numerical method expression. Nodal velocity, e.g., dx/dt of i,j, includes a difference (numerical method) or differential (analytical method) with respect to time j. Nodal acceleration is the second derivative of the nodal position performed to get nodal acceleration. It should be understood that the expressions with x extend to y and z directions as well. For example the position has x, y and z components, e.g., $X_{i,j}$, $Y_{i,j}$, $Z_{i,j}$.

Bend angle space, e.g., node angular position, angular velocity and/or angular acceleration. Bend angle is illustrated where $P_i$ and $P_{i+1}$ can denote planes drawn through node indexes i and i+1 parallel to a cross section of the optical fiber. Angles may be in multiple axes. Here, the computation can be analytical or numerical as described above. The angular position may be expressed as a formula (analytical) or nodal elements (numerical). The velocity is a first derivative or difference, and the acceleration is a second derivative or second difference of the position relationship.

Twist or twist-derived parameters (these include twist, roll, pitch yaw, torsion, etc.). Twist will be referred to herein as a catch-all descriptor for curving in three dimensions (Pitch, Roll, Yaw). Twist can be defined as any rotation (roll, pitch and/or yaw) of the local coordinate systems between node locations. Twist is the effect descriptive of the wobble/pitch/frequency of rotation of the fiber cores of the shape sensing device.

Temporal filtering such as temporal averaging, with or without filter thresholds.

Processing based on additional prior knowledge or other computational models 142 which capture spatio-temporal constraints on instrument position and dynamics, e.g., velocity, acceleration, or shape evolution. These models 142 may include possible shape configuration that are possible for the optical fibers. Shapes that exceed these models (plus a tolerance) may be deemed unacceptable or erroneous. For example, a model may include a unit length of the shape sensing system 104. Due to its geometry, (e.g., its thickness) a radius of less than 1.0 mm may not be physically possible. If the shape sensing data results in a kink that exceeds this radius, high confidence would exist that the data is erroneous and can be eliminated.

Any combination of the above parameters may be employed as well as others. For example, the bend angle parameters may be employed for a gradual bending section of the fiber while the twist parameters may be employed for a spiralling section of the same fiber.

Other parameters including statistical or historic parameters may be employed (such as, e.g., a positive prediction based on previously observed shapes).

Using a combination of the above parameters provides the best results. It should be understood that the optical fiber system is modeled based upon a series of nodes placed along a length of the optical fiber. These nodes are monitored to obtain relative distances and positions with respect to other nodes on the same optical fiber or between optical fibers or to a reference system.

The stability module 140 can be run in real-time, this may be important for some applications such as cardiac interventions (where the heart is beating). In one example, when a portion of a shape (distal) is erroneous while a proximal shape is accurate, the stability module 140 can detect the fiber index/node where the instability arises, and display a portion of the shape and/or correct the reminder of the shape and display the correct shape and/or display an earlier correct shape for the incorrect portion. The stability module 140 may run in real-time during a procedure or may be switched off. Implementations of the stability module 140 is shown and described with respect to FIGS. 2 and 7.

Figure 2:
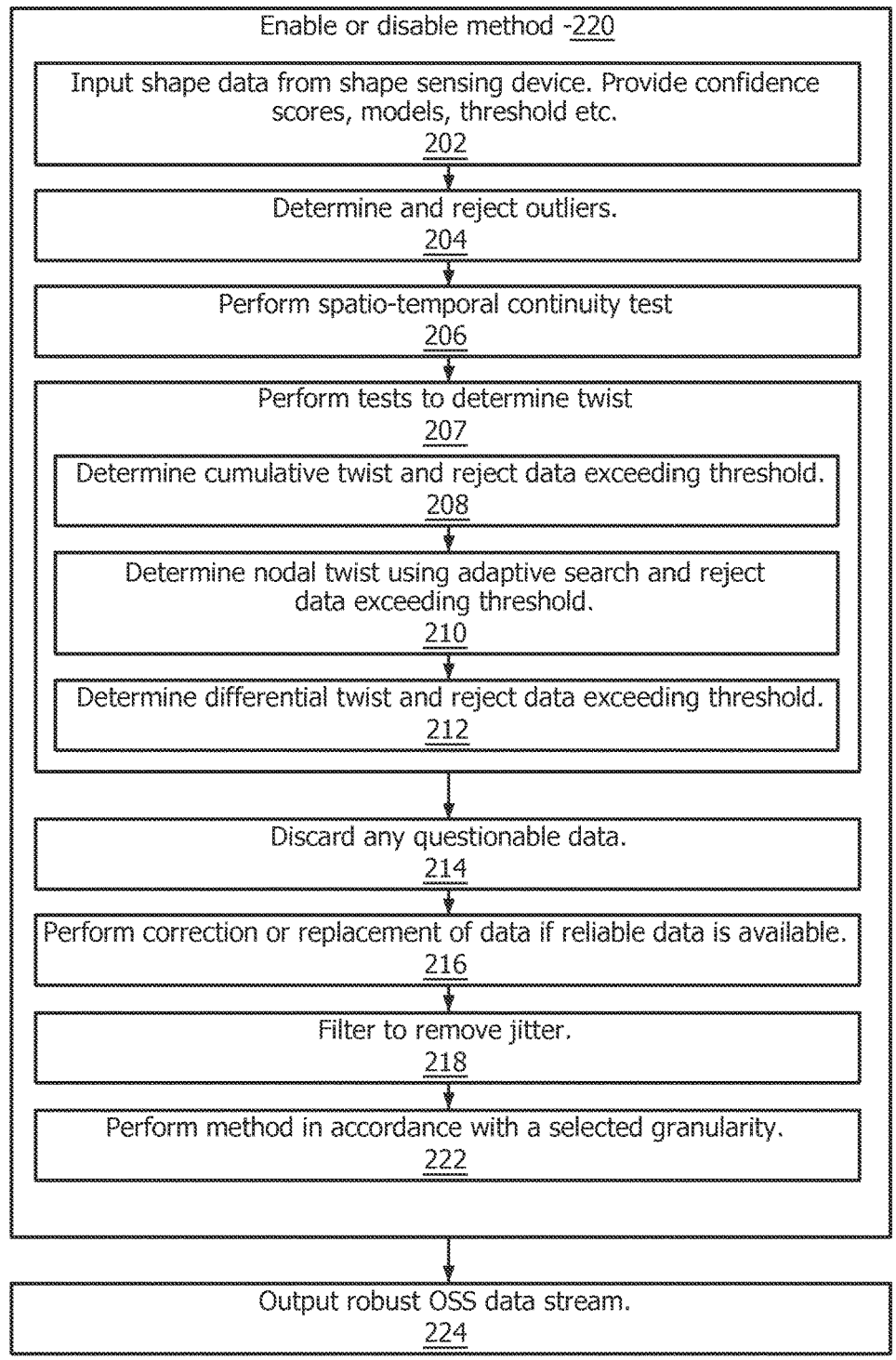
FIG. 2 is a block/flow diagram showing a shape sensing method performed by the stability module in accordance with one illustrative embodiment.

Referring to FIG. 2, a method for detecting whether a shape is acceptable (or accurate) or unacceptable (or inaccurate) is provided. The method described is illustrative of one set of tests that may be run. It should be understood that other combinations of tests or different tests may be employed. The method then may modify an output shape measurement stream to correct the stream in accordance with one embodiment. In block 202, shapes are read from the fiber optic shape sensing instrument (104). Confidence measures, models or thresholds are assigned for different parameters to provide criteria for checking continuity, twist or other geometric features. Models or training data may be employed to compare with shape data. In one example, a test, in simple form, may include using a training dataset, and based on the information gained from an OSS system, "ROC curves", i.e., receiver operator characteristics curves, are generated. ROC curves are employed to plot true positive rate (TPR) against false positive rate (FPR). Based on a comparison between the training data and measure data, the ROC curves may be employed to optimize and calibrate thresholds based on performance. This permits the selection of a best model for evaluating OSS curves, or may be employed to select a most likely shape of the OSS.

For example, one test could optimize for sensitivity, and another test could optimize for specificity, or yet another may employ a combination of TP/FP (true positive/false positives) between the measured data and the training dataset. Sensitivity and specificity are statistical measures of the performance of a binary classification test, also known in statistics as classification functions. Sensitivity measures the proportion of actual positives which are correctly identified. Specificity measures the proportion of negatives which are correctly identified. By plotting sensitivity versus specificity between a model and the measured data, a most likely shape can be determined. As an example, a measured shape is compared to a plurality of models (e.g., an adaptive search) using ROC curves to determine a highest confidence fit for the shape. The model with the best fit is most likely the true shape, which may include a well-known shape pattern normally taken by the device. This shape is compared to the measured data to identify likely erroneous data which can now be flagged. If no model is found with sufficient confidence, the shape is rejected or flagged for further testing. Other criteria or thresholds may include true negatives, positive predictive value (PPV), etc. Other methods for identifying erroneous data by employing models, statistics, etc. are also contemplated.

Figure 3:
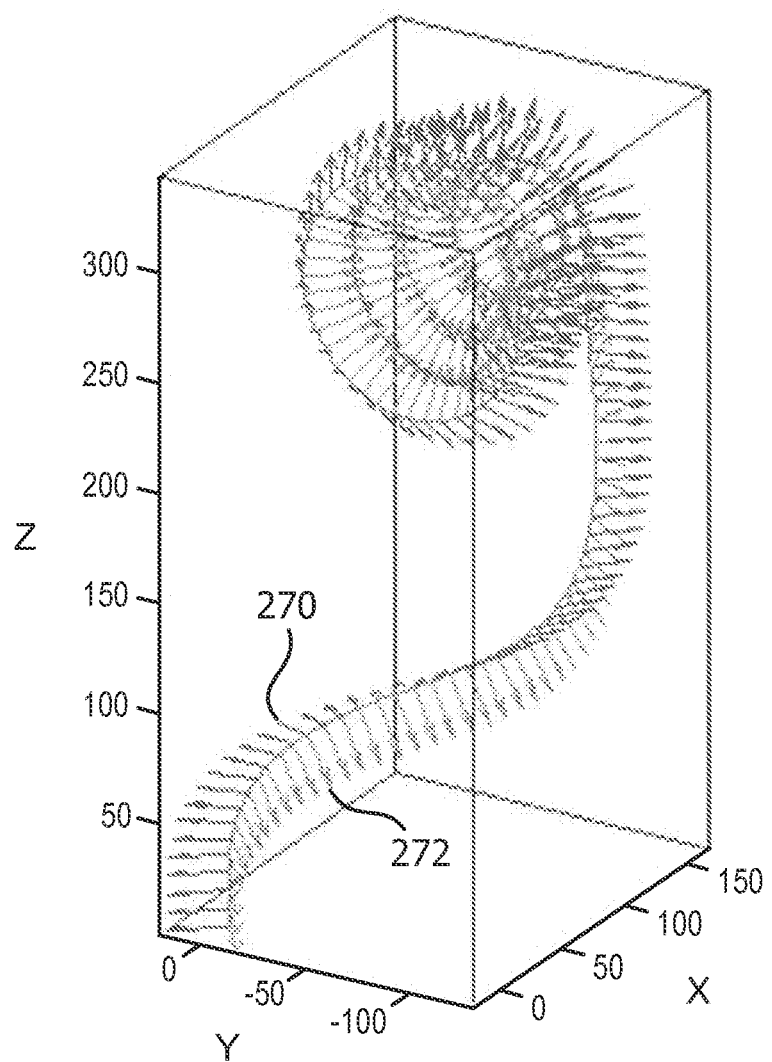
FIG. 3 is a plot showing two perpendicular orientation vectors corresponding to nodal positions for quantifying twist in accordance with one illustrative embodiment.

In block 204, the data is checked for gross outliers from prior data, and the outliers are rejected (e.g., stray points or data). This may include computing a distance measure from other data, e.g., a Euclidean distance or the like. If the distance exceeds a threshold, the outlier can be deleted. Outliers may be obvious in relation to other data and may be filtered out. In block 206, spatio-temporal continuity is computed, tested and reviewed. This may include comparing measured data to expected data from a model or from a previously obtained shape. If the spatio-temporal continuity is poor (e.g., does not meet a threshold set for such continuity), then the shapes or portions thereof are rejected or tagged for rejection later. Continuity can be checked as a node-by-node comparison to determine if the data collected is geometrically possible, if data is missing, etc. Cusps or other inconsistencies can be identified and eliminated from the dataset In block 207, OSS positional twist is measured/computed. This may include reading in nodal position and orientation data from the OSS device. Two perpendicular orientation vectors 270 and 272 may be generated based on the position and orientation data as depicted in FIG. 3. A change in orientation between adjacent or nearby points can be employed to estimate twist, torsion, roll, etc. In one embodiment, an approximation of twist or a twist related parameter is computed by taking a dot product between one orientation vector (e.g., 272) at a first location and another orientation vector (e.g., 272) at a nearby or neighboring location. A difference provided by the dot product indicates a change in twist over a distance between the locations. Other computations and measures are also contemplated. The twist may be computed or quantified in other ways as well. For example, in block 208, nodal data is accumulated to measure cumulative twist for the shape sensing device. Cumulative twist is the amount of twist built up over a length of optical fiber. This measure is compared to a threshold based on a maximum cumulative twist (e.g., per unit length, etc.). If the maximum accumulated twist is exceeded by the shape, the data exceeding the threshold is rejected.

In block 210, an adaptive search may be performed to compare a maximum of nodal twist or roll to, e.g., a constant (k) times a standard deviation of overall twist. This handles more local twisting scenarios. If the local twist is beyond the limit then node segments are rejected. The adaptive search assists in determining whether a geometrical twist is even possible by comparing the geometry with an acceptable statistical model or models (hypothesis test). Given bending radius limitations of fiber optic devices, certain twists or rolls are simply not possible and the data associated with these can be eliminated.

In block 212, a differential twist (e.g., derivative of the positional twist curve) may be performed to verify special events. The twist differential may include a derivative of the twist curve. In one example, a determination of whether a shape beyond a portion of a big jump (e.g., a peak or large change in the data) is reliable may be computed. This may include a cross-validation with the maximum cumulative twist to see if consistency exists between the two measures and to verify the geometry of the OSS fibers.

In block 214, if there is any doubt in any step that the data (shape at that instant) is not reliable the data is discarded. This is to ensure a very high false negative, even if it compromises the false positive. Discarded data may be employed for model building or other purposes.

In block 216, correction of data may include replacing unreliable data with previously collected reliable data. For example, if reliable, a portion or shape is registered to a corresponding portion of a good shape at a previous instant of time (e.g., using point cloud computations of nodal data). This operates as an additional check using a same number of points in both the current and previous versions for registration of the two data sets. Erroneous segments (e.g., rejected segments) are therefore replaced with previously collected valid segments or other data (e.g., extrapolated data) to reconstruct a shape.

In block 218, forward prediction (e.g., Kalman filtering or other filtering method) towards the distal tip of the shape sensing device may be performed for correction of jitter. Forward prediction attempts to predict a data sample from previous data samples. Differences may be deciphered as jitter and can be filtered out to improve a shape sensing trace.

In block 220, the stability module may be enabled or disabled by a user feature enabling clinician to decide when to use and when not to use the method. In block 222, the method may be executed segment by segment, node by node, section by section or any other useful granularity. The segments, etc. may be individually rejected according to the selected granularity, which may also lead to the rejection of larger portions. It should be understood that the present examples are not limiting as other useful tests may be employed. In addition, not all of the steps of FIG. 2 need to be employed to determine a robust dataset for shape sensing data. In block 224, a robust OSS data stream, data set, measurements, etc. are output from the stability module (140).

Figure 4:
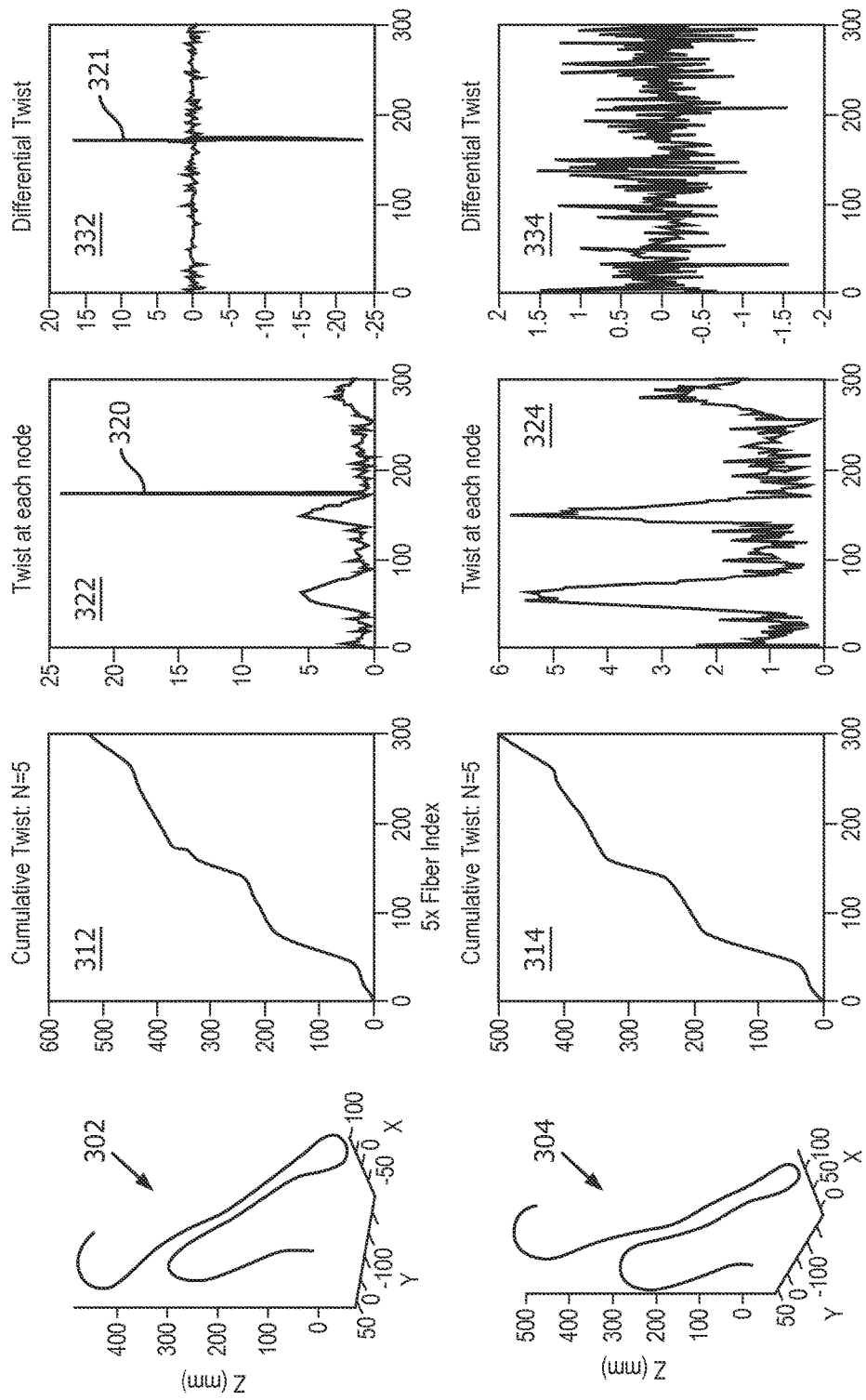
FIG. 4 is a diagram showing images having bad shape data and good shape data along with images for twist in accordance with one illustrative embodiment.

Referring to FIG. 4, an illustrative example of data set processing is shown in accordance with one example. A roll/twist based correction is shown in one implementation used for distinguishing good shapes from bad shapes, which is not obvious by merely looking at the positions and orientations of the OSS in plots 302 and 304. Plots 302 and 304 show two shapes, one good (304) and one bad (302). A twist/roll based approach for detection and correction of the same is handled as follows. Plots 312, 322 and 332 correspond to the plot 302, and plots 314, 324 and 334 correspond to the plot 304. Plots 302 and 304 show position in the x, y and z directions. Plots 312 and 314 are plots of cumulative twist at 5 times the node index of the fiber. Plots 322 and 324 are plots of nodal twist, e.g., the twist at each node relative a previous node versus node index number. Plots 332 and 334 show differential (derivative) of nodal twist (plots 322 and 324) plotted against node index number. All plots skip to every fifth node for clearer visibility with a decimation of 100. For the bad shape 302, a sharp peak 320, 321 in the nodal twist plot 322 and differential twist plot 324 can be seen. Rather than eliminating this shape, the differential twist can be used to detect the fiber nodal index where failure occurs and, in this case, conclude that the shape before as well as after that index are good. This can then be used to properly register or re-align the incorrect portion of the bad shape (using a prior good shape or interpolating) thereby performing real-time correction and providing stability.

Figure 5:
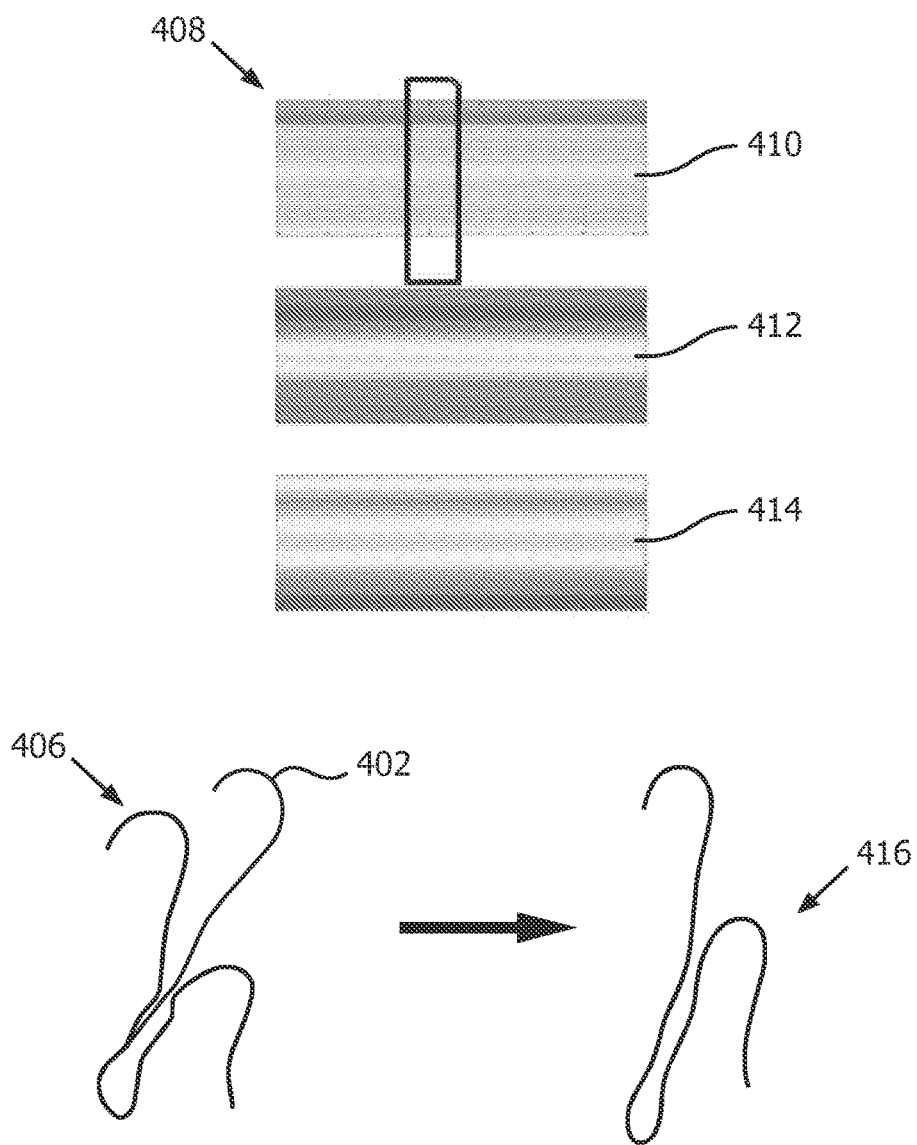
FIG. 5 is a diagram showing a verification method using images collected using computed tomography (CT) to check shape sensing data in accordance with one illustrative embodiment.

Referring to FIG. 5, verification methodologies may be performed to test the method and check the reliability of shape sensing data. In one embodiment, verification may be performed using imaging (imaging system 110, FIG. 1). In one embodiment, an image is collected using, e.g., a computed tomography (CT) setup in which an OSS fiber is visible in the CT image. The setup employs a CT scanner to generate a surview scan of the OSS fiber in, e.g., an angiogram phantom image. OSS shapes after 3 minutes of recording and rejection of gross outliers is generated in an image 406. By comparing, the image 406 with the CT scan, a section 402 is inconsistent and flagged for elimination. Another method is employed to verify these results. This method checks for spatio-temporal continuity as shown in image 408. Image 408 looks at nodal positions along the OSS fiber in x, y and z coordinates. A bad shape will show up in the image 408 as a different pattern, and in an ideal case a smooth color map is generated as depicted in FIG. 5. In image 408, a top plot 410, middle plot 412, and a bottom plot 414 correspond to x, y and z coordinates (with respect to an OSS coordinate system). An image 416 shows final results after the method has performed the correction and eliminated section 402.

In addition to verification, on-line correction may be performed using live imaging, e.g., ultrasound, X-rays, CT, etc. To match the shape of an X-ray image to a shape in OSS, a filtering and registration scheme can be applied. For example, the X-ray image can be enhanced using a vesselness filter and the OSS shape can be registered using a 2D-3D registration scheme. Any discrepancy of the OSS shape can be detected by comparing the registered OSS shape with the imaging data. If the OSS shape is outside the shape in the X-ray, then the OSS shape can be moved or warped to match the image space. This can be performed using image processing 130 of system 100 in FIG. 1. Other image processing techniques may be employed for verification and image correction as well. Verification and image correction may be performed prior to, during and/or after a procedure to provide quality assurance.

Figure 6:
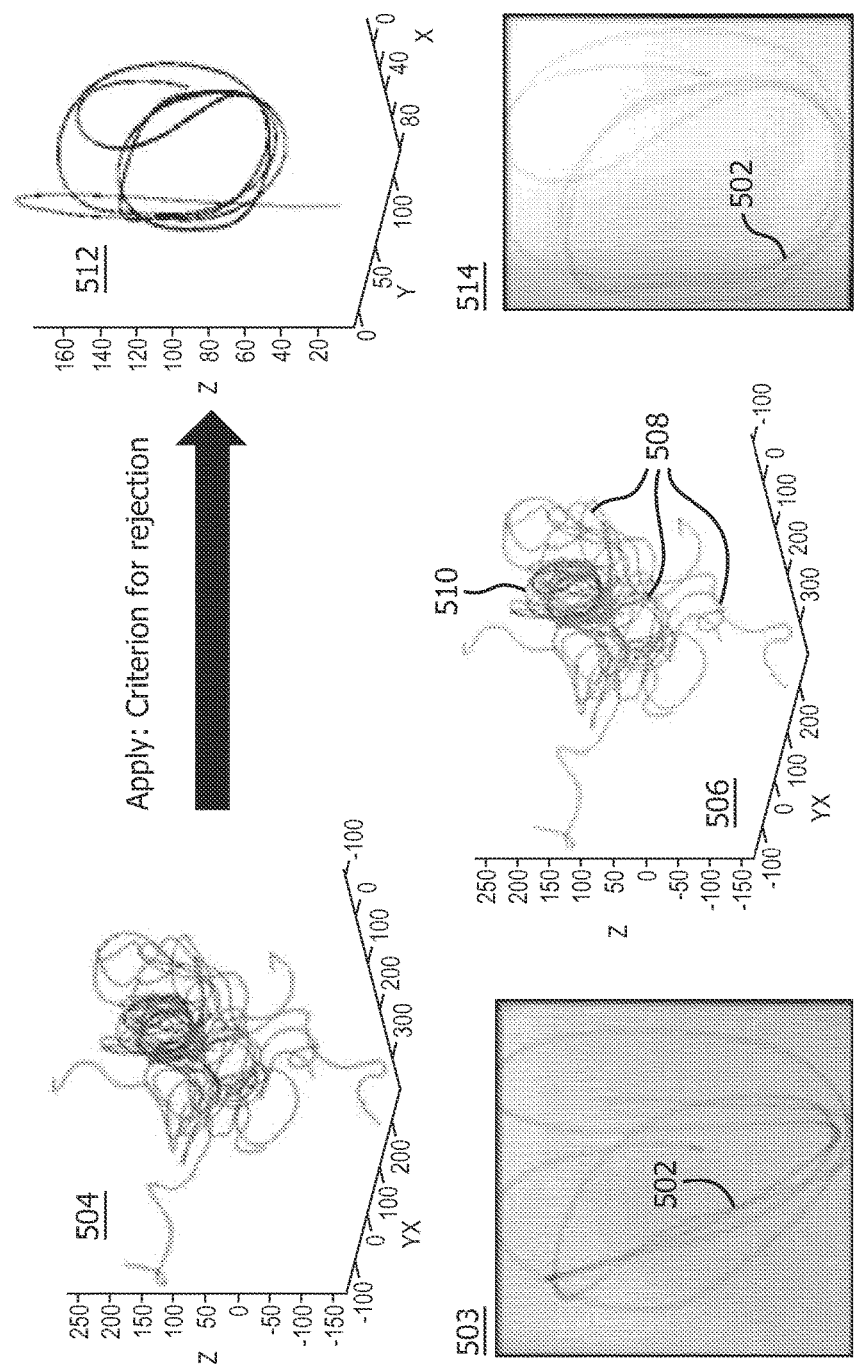
FIG. 6 shows an example of the stability method applied to a coiled optical fiber and conformed using a rotational run (X-ray) in accordance with one illustrative embodiment.

Referring to FIG. 6, an instance of a correction and verification method is shown during a rotational run (X-ray), e.g., using a three-dimensional rotational angiography (3DRA) protocol with an OSS fiber 502 coiled up to fit in the field of view of a biplane cardiovascular X-ray system, in this case a Model FD-10 system available from Philips®. An image 504 shows original shape data of the fiber 502 collected by OSS processing. An x-ray image 503 of the actual fiber is also shown. Another image 506 shows the stability method identifying rejected shapes 508 and accepted shapes 510. The rejected shapes 508 were eliminated by applying criteria for rejection. A final result is shown in image 512. The result in image 512 closely matches the original fiber 502 of image 503. The fiber 502 of image 503 is turned to provide a rotated x-ray image 514. The image 514 matches the orientation of the result image 512. Image 512 and image 514 have a corresponding orientation. Fiber 502 is shown in X-ray projections of the shape during the 3DRA in both images 503 and 514. Application of the stability method in accordance with the present principles results in eliminating 52.7% of the data to provide the correction as shown in image 512.

Figure 7:
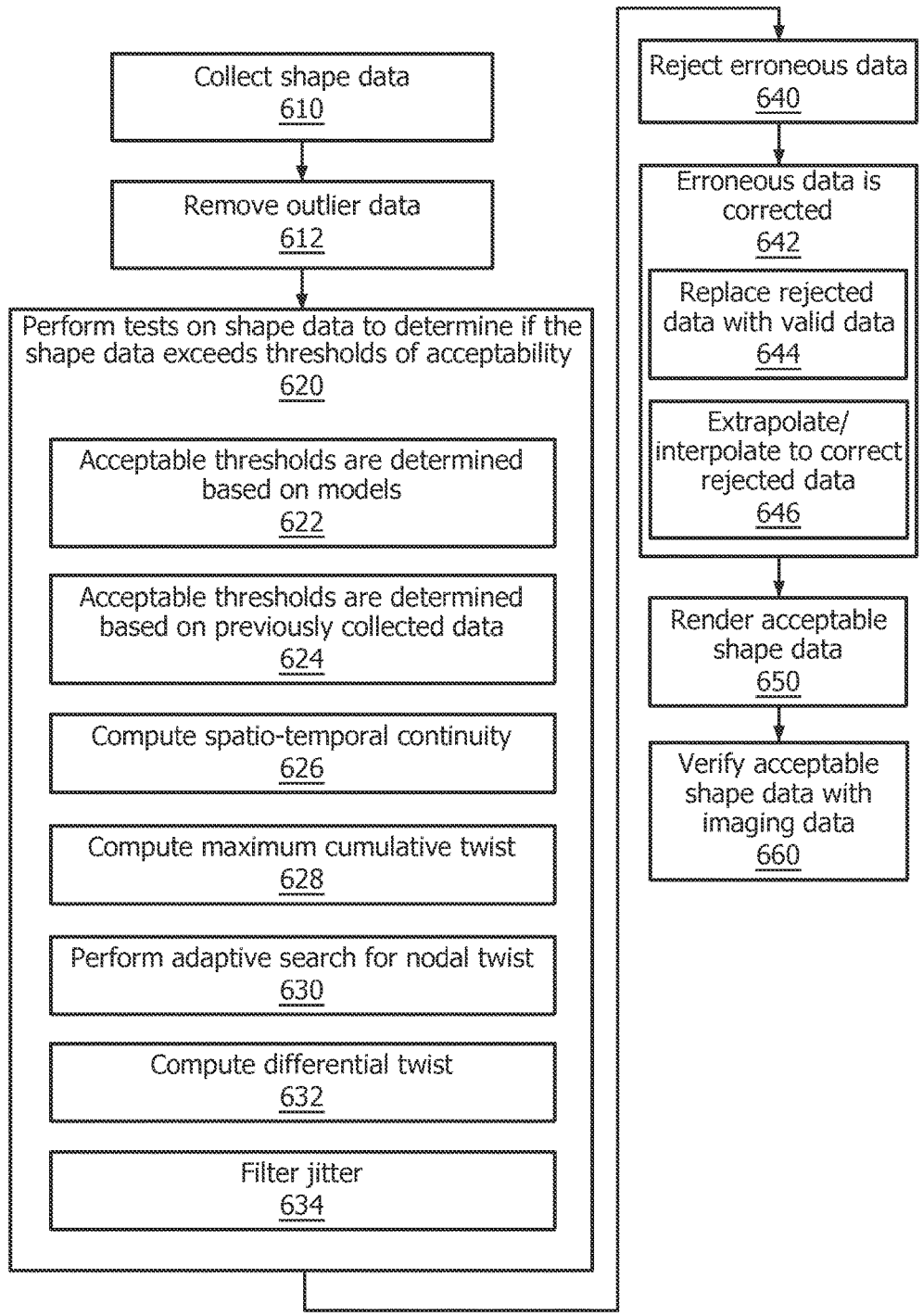
FIG. 7 is a flow diagram showing a method for shape sensing with optical fiber in accordance with an illustrative embodiment.

Referring to FIG. 7, another method for shape sensing with optical fiber is depicted in accordance with the present principles. This method may also be employed using the stability module 140 of FIG. 1. In block 610, shape data from an optical fiber shape sensing device is collected. The data may be collected from a plurality of nodes or nodal points defined along the length of the device or an individual fiber of the device. In block 612, outlier data is removed from the shape data. The outlier data may be defined in a plurality of ways. In a general sense, outliers may include individual data points that appear in the data and are not logically connected to other points. This may include sets of data or entire segments of the collected data set.

In block 620, a test or tests are performed on the shape data to determine data positions that exceed an acceptable threshold based on geometrical expectations of the shape data. Such tests may include hypothesis tests which compare measured data to training data or models. Thresholds may account for geometric impossibilities, safe bending radii, etc. In addition, information about a structure in which the shape sensing device is contained may be employed as a model or to provide thresholds or constraints on geometrically possible configurations. In one embodiment, the thresholds represent a confidence score either set by default, by a constraint or by a user to account for a confidence that the shape data is valid. In block 622, the acceptable thresholds are determined based upon a shape sensing model (e.g., a statistical model, a physiological model, etc.). In block 624, the acceptable thresholds are determined based upon previous collected shape data. This may include data collected at a same location but at a different time.

In block 626, one test on the shape data may include computing spatio-temporal continuity along the shape data. This may include a node by node check in each coordinate axis to determine if the nodes are continuous. If a discontinuity exists, the discontinuous nodes will be tagged. In block 628, another test on the shape data may include computing twist, e.g., a maximum cumulative twist along the shape data, etc. Certain twists or rolls are not possible due to the material and dimensions of the shape sensing device, and due to a volume containing the shape sensing device. Also since the shape sensing device includes optical fibers, exceeding certain bending radii will cause the shape sensing device to fail or not provide reasonable results. Node twisting is computed to determine if an impossible or unlikely twist is being measured. If the twist can be so determined, the sensor data can be tagged.

In block 630, another test on the shape data may include performing an adaptive search of nodal twist or roll between nodes in the shape data to compare to expected limits. This compares a shape of a twist to a data base of shapes to determine in the twist is possible (within a confidence limit). If the twist exceeds a threshold the data is tagged. In block 632, another test on the shape data may include computing a differential twist along the shape data. This test looks at peaks or spikes in the data by differentiating the nodal twist data from block 630. This result can be compared to the accumulated twist as well. In block 634, jitter or other effects are filtered out. Other tests may also be performed in addition to or instead of those described herein.

In block 640, the shape data corresponding to the data positions that exceed an acceptable threshold (erroneous data) are rejected. These include data that has been tagged as falling outside of the acceptable thresholds. Some of this data can be corrected or replaced. In block 642, erroneous shape data is corrected. In block 644, the shape data may be reconstructed by replacing rejected shape data with valid data. The valid data may be from a model or from previously collected acceptable data. In block 646, the rejected shape data may be replaced by extrapolating or interpolating other acceptable data. This permits the reconstruction or patching of rejectable data in a dataset without rejecting a larger amount of data.

In block 650, acceptable shape data is rendered to provide a stable shape sensing data set. This may include displaying acceptable shape data on a display, storing stable shape sensing data or employing stable shape sensing data for a given application. In block 660, the shape data may be verified by comparing the shape data to data collected by an imaging system. Other verification techniques are also contemplated.

In interpreting the appended claims, it should be understood that:
a) the word "comprising" does not exclude the presence of other elements or acts than those listed in a given claim;
b) the word "a" or "an" preceding an element does not exclude the presence of a plurality of such elements;
c) any reference signs in the claims do not limit their scope;
d) several "means" may be represented by the same item or hardware or software implemented structure or function; and
e) no specific sequence of acts is intended to be required unless specifically indicated.

Having described preferred embodiments for systems and methods for stabilizing optical shape sensing (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A method for shape sensing with optical fiber, comprising:
providing an optical fiber shape sensing device having at least one optical fiber;
providing a shape sensing system that includes a workstation comprising a processor, a memory coupled to the processor, and a stability module stored in the memory;
collecting optical signals from the optical fiber shape sensing device and interpreting, by the shape sensing system, the optical signals to determine shape data for the optical fiber shape sensing device;
performing, by the stability module, a test on the shape data for the optical fiber shape sensing device including performing an adaptive search of nodal twist between nodes in the shape data to compare to expected limits, wherein the stability module is configured to determine data positions that exceed an acceptable predetermined threshold which is based on safe bending radii for the optical fiber shape sensing device;
rejecting the shape data corresponding to the data positions that exceed the acceptable predetermined threshold by the stability module; and
rendering acceptable shape data to provide a stable shape sensing data set by the stability module,
wherein a shape of the optical fiber shape sensing device is generated and displayed based on the stable shape sensing data set.

2. The method as recited in claim 1, wherein the acceptable predetermined threshold is determined based upon a shape sensing model.

3. The method as recited in claim 1, wherein the acceptable predetermined threshold is determined based upon previously collected shape data.

4. The method as recited in claim 1, wherein performing a test on the shape data includes computing spatio-temporal continuity along the shape data.

5. The method as recited in claim 1, wherein performing a test on the shape data includes computing a maximum cumulative twist along the shape data.

6. The method as recited in claim 1, wherein the shape data is further tested by computing a differential twist along shape data to identify a node where failure occurs.

7. The method as recited in claim 1, further comprising: reconstructing the shape data by replacing rejected shape data with valid data.

8. The method as recited in claim 7, wherein replacing rejected shape data includes employing previously collected acceptable data.

9. The method as recited in claim 1, wherein rejecting the shape data includes interpolating or extrapolating acceptable data.

10. The method as recited in claim 1 further comprising: using the stable shape sensing data set to generate an image of a shape of the optical fiber shape sensing device, and displaying the image.

11. The method as recited in claim 1, further comprising: verifying the shape data by comparing the shape data to data collected by an imaging system.

12. A method for shape sensing with optical fiber, comprising:
providing an optical fiber shape sensing device having at least one optical fiber;
providing a shape sensing system that includes a workstation comprising a processor, a memory coupled to the processor, and a stability module stored in the memory;
determining, by the shape sensing system, shape data for the optical fiber shape sensing device;
removing, by the stability module, outlier data from the shape data;
testing, by the stability module, the shape data testing includes performing an adaptive search of nodal twist between nodes in the shape data to compare to expected limits to determine data positions that exceed acceptable predetermined thresholds which are based on safe bending radii for the shape sensing optical fiber device, the testing also includes one or more of:
computing spatio-temporal continuity along the shape data; and
computing a twist or a twist-derived parameter along the shape data;
rejecting the shape data corresponding to the data positions that exceed acceptable predetermined thresholds by the stability module; and
rendering acceptable shape data to provide a stable shape sensing data set by the stability module,
wherein a shape of the optical fiber shape sensing device is generated and displayed based on the stable shape sensing data set.

13. A shape sensing system, comprising:
a workstation configured to receive optical signals from a shape sensing enabled device having at least one optical fiber and to interpret the optical signals to generate shape data by determining a shape of the shape sensing enabled device, the workstation including:
a processor;
a memory coupled to the processor; and
a stability module stored in the memory and configured to perform tests on the shape data includes performing an adaptive search of nodal twist between nodes in the shape data to compare to expected limits to determine data positions that exceed an acceptable predetermined threshold which is based on safe bending radii for the shape sensing enabled device, and reject the shape data corresponding to the data positions that exceed the acceptable predetermined threshold for rendering as a stable shape sensing data set,
wherein a shape of the shape sensing enabled device is generated and displayed based on the stable shape sensing data set.

14. The method of claim 1, wherein the shape sensing enabled device comprises a medical device advanced into a volume or subject to determine a shape of the volume or subject.

15. The method of claim 12, wherein the shape sensing enabled device comprises a medical device advanced into a volume or subject to determine a shape of the volume or subject.

16. The system of claim 13, wherein the shape sensing enabled device comprises a medical device advanced into a volume or subject to determine a shape of the volume or subject.

17. The method of claim 1, wherein the shape sensing enabled device comprises a device advanced into a volume to determine a shape of the volume.

18. The method of claim 12, wherein the shape sensing enabled device comprises a device advanced into a volume to determine a shape of the volume.

19. The system of claim 13, wherein the shape sensing enabled device comprises a device advanced into a volume to determine a shape of the volume.

* * * * *